United States Patent [19]

Brown et al.

[11] 4,298,742

[45] Nov. 3, 1981

[54] ESTERS OF BENZOXA(THIA)ZOLE-2-CARBOXYLIC ACIDS

[75] Inventors: Richard E. Brown, East Hanover, N.J.; Vasil St. Georgiev, New Rochelle; Bernard Loev, Scarsdale, both of N.Y.

[73] Assignee: USV Pharmaceutical Corporation, Tuckahoe, N.Y.

[21] Appl. No.: 149,079

[22] Filed: May 12, 1980

[51] Int. Cl.$^3$ .................. A61K 31/42; A61K 31/425; C07D 263/34; C07D 277/68
[52] U.S. Cl. .................. 548/152; 548/317; 424/270; 424/272
[58] Field of Search .................. 548/217, 152

[56] References Cited

U.S. PATENT DOCUMENTS 3,895,022  7/1975  Moller et al. .................. 548/217

FOREIGN PATENT DOCUMENTS 2164851  7/1973  Fed. Rep. of Germany ...... 548/217

OTHER PUBLICATIONS

Gilchrist, et al., "J. Chem. Soci. Comm.," 1975, pp. 962–963.
Dickore et al., "Ann Chem.," vol. 733, (1970), pp. 70–87.

Primary Examiner—Anton H. Sutto
Attorney, Agent, or Firm—Ernest B. Lipscomb, III; Leon E. Tenenbaum

[57] ABSTRACT

New benzoxazole-2-carboxylic acid esters are described. These compounds are useful as anti-allergic reagents.

14 Claims, No Drawings

ESTERS OF BENZOXA(THIA)ZOLE-2-CARBOXYLIC ACIDS

This invention relates to new anti-allergy agents and more particularly to certain heterocyclic esters of improved anti-allergy activity of particular use in the treatment of asthma.

Benzoxazole-2-carboxylic acid esters have been described in the literature. For example, esters wherein the esterifying group is alkyl, phenyl, chlorophenyl and allyl including such esters as are substituted in the benzenoid ring with such groups as alkoxy, nitro, alkyl, phenyl and chloro, are described in *Lieb Ann. Chem.* 733, 70–87 (1970); ibid 749, 1–11 (1971); German Offenlegungschrift No. 2,164,851; and *J. Chem. Soc. Chem. Comm.* 24, 962–3 (1975).

It has now been surprisingly found that certain new esters of benzoxazole-2-carboxylic acid and benzthiazole-2-carboxylic acid have potent anti-allergy activity.

The compounds of the present invention are esters of benzoxazole-2-carboxylic acid and benzthiazole-2-carboxylic acid in which the esterifying group is alkoxyalkyl, aryloxyalkyl, heterocyclealkyl, aminoalkyl or aminoalkoxyalkyl. The benzenoid ring of the said esters may be unsubstituted or substututed with a variety of substituents such as alkyl, nitro, carboxy, alkoxy, halogen, cyano, carbalkoxy and trifluoromethyl, preferably with no more than two such substituents.

The new esters of this invention are represented by the following formula:

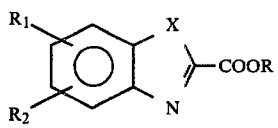

wherein,

X is S or O;

$R_1$ and $R_2$ are each H, $R_3$, $OR_4$, halogen, cyano, $COOR_4$, methanesulfonyl, nitro, trifluoromethyl or taken together, methylenedioxy, wherein $R_3$ is lower alkyl or cycloalkyl of 3 to 7 carbon atoms and $R_4$ is hydrogen or lower alkyl; and R is $-Z-O-R_3$; $-Z-N(R_5R_6)$; $Z^1-O-Z^2-N(R_5R_6)$; $-Z-$ heterocycle; $-Z_1-O-Z_2-$ heterocycle; or $-Z-O-C_6H_4R_1$ wherein each of $R_5$ and $R_6$ are hydrogen or lower alkyl or where taken together with the nitrogen to which they are attached $R_5$ and $R_6$ form a nitrogen-heterocyclic ring, e.g., piperidine, morpholine, piperazine, pyrrole, imidazole, triazoles, dioxazoles, isoxazine, and the like, $R_1$ and $R_3$ have the meaning hereinbefore described, Z, $Z^1$ and $Z^2$ are each a branched or unbranched alkylene chain containing from 2 to about 6 carbon atoms of the principal chain and a total of up to about 12 carbon atoms; $Z^1$ and $Z^2$ when taken together with a hetero atom form a saturated heterocyclic ring; and heterocycle represents a heterocyclic ring containing one or more of the hetero atoms, oxygen, nitrogen and sulfur.

The benzoxazole esters, which up to the present are preferred, are of the formula:

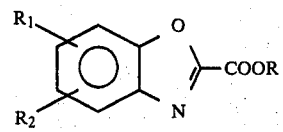

wherein, $R_1$ and $R_2$ are each H, $R_3$, $OR_4$, halogen, cyano, $COOR_4$, methanesulfonyl, nitro, trifluoromethyl or taken together, methylenedioxy, wherein $R_3$ is lower alkyl or cycloalkyl of 3 to 7 carbon atoms and $R_4$ is hydrogen or lower alkyl; and R is $-Z-O-R_3$; $-Z-N(R_5R_6)$; $Z^1-O-Z^2-N(R_5R_6)$; $-Z-$heterocycle; $-Z^1-O-Z^2-$heterocycle; or $-Z-O-C_6H_4R_1$ wherein each of $R_5$ and $R_6$ are hydrogen or lower alkyl or when taken together with the nitrogen to which they are attached $R_5$ and $R_6$ form a nitrogen heterocyclic ring, e.g., piperidine, morpholine, piperazine, pyrrole, imidazole, triazoles, dioxazoles, isoxazine, and the like, $R_1$ and $R_3$ have the meaning hereindescribed, Z, $Z^1$ and $Z^2$ are each branched or unbranched alkylene chain containing from 2 to about 6 carbon atoms in the principal chain and a total of up to about 12 carbon atoms, and $Z^1$ and $Z^2$ when taken together with a hetero atom form a saturated heterocyclic ring.

The heterocyclic ring systems intended for the substituents, $-Z-$heterocycle and $-Z^1-O-Z^2-$heterocycle, include a wide variety of heterocyclic radicals which contain as hetero atom, one or more sulfur, nitrogen, and/or oxygen atoms. These radicals are joined to the alkylene chain represented by Z through a carbon atom of the ring. The rings include unsaturated and saturated heterocyclics, for example, thiophene, furan, pyrrole, pyrrolidine, tetrahydrofuran, benzothiophene, thiazole, benzothiazole, pyridine, piperidine, morpholine, pyran, quinoline, and similar such compounds. The heterocyclic ring can be substituted with various substituents as enumerated herein for radicals $R_1$ and $R_2$.

The benzthiazole esters of the invention are, of course, the sulfur analogs of the benzoxazole esters.

The new benzoxazole esters of this invention are conveniently prepared in a two-step synthesis from the corresponding benzoxazinediones of the following formula:

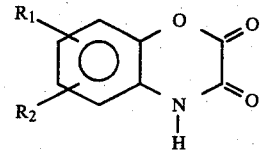

by reaction with thionyl chloride to give the chloro derivative

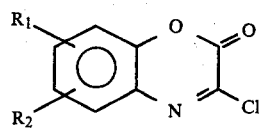

which on reaction with ROH provides the new benzoxazole esters of this invention. The benzthiazole esters are prepared in analogous manner.

The esters of the invention are also prepared by ester interchange employing ROH with the corresponding lower alkyl ester, e.g., methyl or ethyl ester.

The starting heterocyclic compounds for the foregoing preparative procedures are known compounds or are preparable by known procedures.

The alcohols of formula ROH employed in the said preparative procedures are those in which R is as defined hereinbefore. Thus, such alcohols include, for example, (a) alkoxyalcohols of the formula: HO—Z—O—$R_3$;
(b) amino alcohols of the formula: HO—Z—$N(R_5R_6)$, and HO—$Z^1$—O—$Z^2$—$N(R_5R_6)$; and
(c) aryloxyalcohols of the formula: HO—Z—O—$C_6H_4R_1$
(d) heterocyclic alcohols of the formulae: HOZ-heterocycle or $HOZ_1$—O—$Z_2$-heterocycle In these formulas for ROH, Z, $Z^1$, $Z^2$, $R_1$, $R_3$, $R_5$ and and $R_6$ have the same meaning as hereinbefore described.

Using the appropriate alcohols with corresponding starting compounds, a wide variety of benzoxazole and benzthiazole esters can be prepared as shown in the following table employing the procedures described:

| X | $R_1$ | $R_2$ | R |
|---|---|---|---|
| O | $C_4H_9$ | H | $(CH_2)_2OCH_3$ |
| O | $COOCH_3$ | H | $(CH_2)_2OC_2H_5$ |
| O | $CF_3$ | H | $(CH_2)_2OC_2H_5$ |
| O | $NO_2$ | H | $(CH_2)_2O(CH_2)_3NHCH_3$ |
| S | Cl | H | $(CH_2)_2NHCH_3$ |
| S | H | H | $(CH_2)_3OC_6H_5$ |
| O | COOH | Cl | $(CH_2)_2OC_4H_9$ |
| O | $OCH_3$ | $OCH_3$ | $(CH_2)_4OCH_3$ |
| O | Cl | Cl | $(CH_2)_4ON(CH_3)_2$ |
| S | $NO_2$ | H | $(CH_2)_4NH_2$ |
| S | $CH_3$ | OH | $(CH_2)_2OC_2H_5$ |
| O | Cl | H | $(CH_2)_2OC_6H_5$ |
| O | Cl | H | $(CH_2)_2OC_6H_4CH_3$ |
| S | Cl | $OCH_3$ | $(CH_2)_2OC_3H_7$ |
| S | $CH_3$ | $OCH_3$ | $(CH_2)_2OC_3H_6NH_2$ |
| O | $CH_3$ | $NO_2$ | $(CH_2)_2OC_2H_5$ |
| O | $C_3H_7$ | H | $(CH_2)_2NHC_4H_9$ |
| O | $CF_7$ | H |  |
| O | $OCH_3$ | $OCH_3$ | 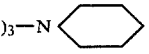 |
| O | F | H | $(CH_2)_3-N\langle\rangle$ |

The present new heterocyclic esters are therapeutically useful as such or can be employed in the form of salts with a wide variety of acids, inorganic and organic, including therapeutically-acceptable acids. The salts with therapeutically-acceptable acids are, of course, useful in the preparation of formulations where water solubility is desired. The salts with therapeutically-unacceptable acids are particularly useful in the isolation and purification of the present new esters. Therefore, all acid salts of the present new esters are contemplated by the present invention.

The pharmaceutically-acceptable acid addition salts are of particular value in therapy. These include salts of mineral acids such as hydrochloric, hydriodic, hydrobromic, phosphoric, metaphosphoric, nitric and sulfuric acids, as well as salts of organic acids such as tartaric, acetic, citric, malic, benzoic, glycollic, gluconic, gulonic, succinic, arylsulfonic, e.g., p-toluenesulfonic acids, and the like. The pharmaceutically-unacceptable acid addition salts, while not useful for therapy, are valuable for isolation and purification of the new substances. Further, they are useful for the preparation of pharmaceutically-acceptable salts. Of this group, the more common salts include those formed with hydrofluoric and perchloric acids. Hydrofluoride salts are particularly useful for the preparation of the pharmaceutically-acceptable salts, e.g., the hydrochlorides, by solution in hydrochloric acid and crystallization of the hydrochloride salt formed. The perchloric acid salts are useful for purification and crystallization of the new products.

The present new compounds form conjugates with amino acids and the sugar acids. For example, conjugates can be formed with glucuronic acid, e.g., β-D-glucuronic acid, as well as amino acids especially alpha amino acids, such as glycine, lysine, cystine, methionine, aspartic acid, alanine and the like. The conjugates with pharmaceutically-acceptable amino acids and glucuronic acid are especially useful in formulation of therapeutic dosage forms.

As therapeutic agents, the present new heterocyclic esters are particularly useful as anti-allergy agents, acting via inhibition of mediator release. These esters are active orally in the passive cutaneous anaphylaxis (PCA) screen; and inhibit histamine release from passively sensitized rat mast cells.

The therapeutic agents of this invention may be administered alone or in combination with pharmaceutically-acceptable carriers, the proportion of which is determined by the solubility and chemical nature of the compound, chosen route of administration and standard pharmaceutical practice. For example, they may be administered orally in the form of tablets or capsules containing such excipients as starch, milk sugar, certain types of clay and so forth. They may be administered orally in the form of solutions which may contain coloring and flavoring agents or they may be injected parenterally, that is, intramuscularly, intravenously or subcutaneously. For parenteral administration, they may be used in the form of a sterile solution containing other solutes, for example, enough saline or glucose to make the solution isotonic.

The physician will determine the dosage of the present therapeutic agents which will be most suitable and it will vary with the form of administration and the particular compound chosen, and furthermore, it will vary with the particular patient under treatment. He will generally wish to initiate treatment with small dosages substantially less than the optimum dose of the compound and increase the dosage by small increments until the optimum effect under the circumstances is reached. It will generally be found that when the composition is administered orally, larger quantities of the active agent will be required to produce the same effect as a smaller quantity given parenterally. The compounds are useful in the same manner as other anti-allergy agents and the dosage level is of the same order of magnitude as is generally employed with these other therapeutic agents. The therapeutic dosage will generally be from 10 to 750 milligrams per day and higher although it may be administered in several different dosage units. Tablets containing from 10 to 250 mg. of active agent are particularly useful.

The following examples further illustrate the invention.

EXAMPLE 1

A. 3,6-Dichlorobenzoxazine-2-one

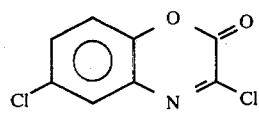

A mixture of 80.5 g. of 6-chlorobenzoxazin-2,3-dione, 40 ml. of thionyl chloride, 15 ml. of dimethyl formamide (DMF) and 1.5 l. of toluene was refluxed with stirring for 5 hours. The reaction mixture was filtered hot and the filtrate concentrated to a gum. Recrystallization from toluene gave product, m.p. 136°-138° C.

B. Ethoxyethyl 5-chlorobenzoxazole-2-carboxylate

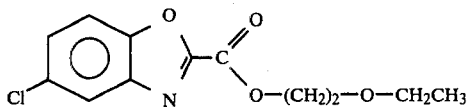

A mixture of 36 g. of the product of Part A and 13.7 g. $Na_2CO_3$ in 250 ml. of ethoxy-ethanol was heated at 70° C. for 14 hours. The solvent was evaporated and the residue extracted with ethyl acetate (200 ml.). The solution was washed with water, dried, decolorized with charcoal and then evaporated to dryness. The residue was recrystallized from ethyl acetatehexane to give crystalline product, m.p. 53°-54° C.

EXAMPLE 2

2-(2-tetrahydropyranyl)ethyl benzoxazole-2-carboxylate

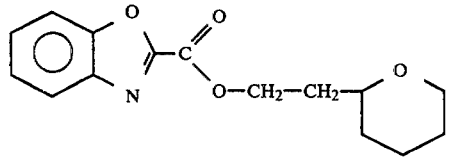

A mixture of 17.7 g (0.1 mole) of methyl benzoxazole 2-carboxylate, 14.3 g (0.11 mole) of 2-(2-tetrahydropropyranyl)ethanol and 0.3 ml of conc. sulfuric acid is refluxed for 4 hours using a Soxhlet extractor filled with 4 A molecular sieves to remove methanol, the mixture poured over ice and the solid product collected by filtration.

In the same way as described above the following products are prepared:

2-(diethylamino)ethyl 5-chloro-benzoxazole-2-carboxylate 3-(4-Methyl-1-piperazinyl)propyl 5,6-dimethoxybenzoxazole-2-carboxylate 2-adamantyloxy-6-methoxy-benzoxazole-2-carboxylate m-chlorobenzyl-5-methyl-benzoxazole-2-carboxylate

EXAMPLE 3

Employing the procedure of EXAMPLE 1, and appropriate starting materials the following benzoxazole-2-carboxylates were prepared:

2-Ethoxyethyl benzoxazole-2-carboxylate (m.p. liquid)

2-Ethoxyethyl 6-methylbenzoxazole-2-carboxylate (m.p. 65°-67° C.)

2-Ethoxyethyl 5-nitrobenzoxazole-2-carboxylate (m.p. 90°-92° C.)

2-Ethoxyethyl 5,6-dimethoxybenzoxazole-2-carboxylate (m.p. 91°-93° C.)

2-Ethoxyethyl benzothiazole-2-carboxylate (m.p. 55°-57° C.)

The compounds of this invention have potent activity in inhibiting the formation of a wheal when screened according to the Rat Passive Cutaneous Anaphylaxis (PCA) Screen as described by I. Mota, Life Sciences, 7, 465 (1963) and Z. Ovary, et al., Proceedings of Society of Experimental Biology and Medicine, 81, 584 (1952).

In addition, the compounds of this invention have potent activity as inhibitors of histamine release from passively sensitized rat mast cells according to the procedure described by E. Kusner, et al., Journal of Pharmacology and Experimental Therapeutics.

The results of the testing of the new compounds of this invention were compared with the results obtained when several of the known alkyl esters of benzoxazole-2-carboxylic acid were tested in the same way. Although the known esters and the new esters of this invention were about equally potent in inhibiting wheal formation in the PCA test, it was surprisingly found that the new esters of this invention were up to 200 times more potent than the known esters in inhibiting histamine release from rat mast cells. The results of this comparison for some of the new esters is summarized in the following chart in which the data is given as $I_{50}$ values, i.e. the dose in micromoles required to achieve a 50% reduction in histamine release as compared to control experiments.

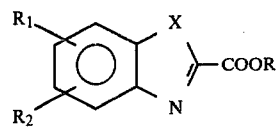

| Cpd. # | X | R | $R_1$ | $R_2$ | RMC ($I_{50}uM$) |
|---|---|---|---|---|---|
| 1 | 0 | Known $CH_3$ | H | H | 140 |
| 2 | 0 | Known $C_2H_5$ | H | H | 100 |
| 3 | 0 | Known $C_4H_9$ | H | H | 1000 |
| 4 | 0 | New $(CH_2)_2OEt$ | H | H | 1000 |
| 5 | 0 | New $(CH_2)_2OEt$ | 6-$CH_3$ | H | 5 |
| 6 | 0 | New $(CH_2)_2OEt$ | 5-$NO_2$ | H | 30 |
| 7 | 0 | New $(CH_2)_2OEt$ | 5-$OCH_3$ | 6-$OCH_3$ | 80 |
| 8 | 0 | New $(CH_2)_2OEt$ | 5-Cl | H | 15 |

What is claimed is:

1. An antiallergic compound of the formula:

wherein,
X is S or O, $R_1$ and $R_2$ are each hydrogen, $R_3$, $OR_4$, halogen, cyano, $COOR_4$, methanesulfonyl, nitro, trifluoromethyl, or taken together methylenedioxy, wherein $R_3$ is lower alkyl or cycloalkyl of 3 to 7 carbon atoms, and $R_4$ is hydrogen or lower alkyl; and R is

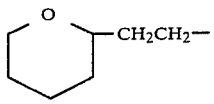

or $-Z-OR_3$ wherein Z is a branched or unbranched alkylene chain containing from 2 to 6 carbon atoms in the principal chain and a total of up to about 12 carbon atoms, and $R_3$ is as defined above, and acid addition salts thereof.

2. An antiallergic compound according to claim 1 wherein X is O.

3. An antiallergic compound according to claim 2 wherein R is

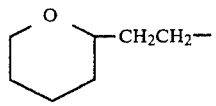

4. The compound according to claim 2 wherein $R_1$ and $R_2$ are each H; and R is $-Z-O-R_3$.

5. The compound according to claim 2 wherein $R_1$ is $CH_3$; $R_2$ is H; and R is $-Z-O-R_3$.

6. The compound according to claim 2 wherein $R_1$ is nitro; $R_2$ is H; and R is $-Z-O-R_3$.

7. The compound according to claim 2 wherein $R_1$ and $R_2$ are $OCH_3$; and R is $-Z-O-R_3$.

8. The compound according to claim 2 wherein $R_1$ is Cl; $R_2$ is H; and R is $-Z-O-R_3$.

9. 2-Ethoxyethyl 5-chlorobenzoxazole-2-carboxylate.

10. 2-Ethoxyethyl 6-methylbenzoxazole-2-carboxylate.

11. 2-Ethoxyethyl 5-nitrobenzoxazole-2-carboxylate.

12. 2-Ethoxyethyl 5,6-dimethoxybenzoxazole-2-carboxylate.

13. 2-Ethoxyethyl benzoxazole-2-carboxylate.

14. 2-Ethoxyethyl benzothiazole-2-carboxylate.

* * * * *